(12) United States Patent
Ohkura

(10) Patent No.: US 6,800,853 B2
(45) Date of Patent: Oct. 5, 2004

(54) ELECTRON MICROSCOPE AND METHOD OF PHOTOGRAPHING TEM IMAGES

(75) Inventor: Yoshihiro Ohkura, Tokyo (JP)

(73) Assignee: Jeol Ltd., Tokyo (JP)

( * ) Notice: Subject to any disclaimer, the term of this patent is extended or adjusted under 35 U.S.C. 154(b) by 0 days.

(21) Appl. No.: 09/991,546

(22) Filed: Nov. 16, 2001

(65) Prior Publication Data

US 2002/0100873 A1 Aug. 1, 2002

(30) Foreign Application Priority Data

Nov. 16, 2000 (JP) ......................... 2000-349222

(51) Int. Cl.⁷ ................. G01N 23/00; G21K 7/00
(52) U.S. Cl. ............... 250/307; 250/309; 250/311
(58) Field of Search .................. 250/307, 309, 250/311, 310

(56) References Cited

U.S. PATENT DOCUMENTS 4,851,674 A * 7/1989 Kobayashi .............. 250/311
4,866,273 A * 9/1989 Kobayashi et al. ......... 250/311
5,300,776 A * 4/1994 Krivanek ................... 250/307
5,304,801 A * 4/1994 Arai .......................... 250/311
5,659,174 A * 8/1997 Kaneoka et al. ........... 250/310

FOREIGN PATENT DOCUMENTS

| JP | 56130066 | 10/1981 |
|---|---|---|
| JP | 63228559 | 9/1988 |

* cited by examiner

Primary Examiner—John R. Lee
Assistant Examiner—Paul M. Gurzo
(74) Attorney, Agent, or Firm—Webb Ziesenheim Logsdon Orkin & Hanson, P.C.

(57) ABSTRACT

In the electron microscope in accordance with the present invention, the electron beam is scanned during a SEARCH mode for searching for a field of view of interest to obtain a TEM image. The state of excitation of the condenser lens does not vary when the mode of operation is switched from the SEARCH mode to a PHOTO mode.

14 Claims, 4 Drawing Sheets

SPECIMEN

ELECTRON MICROSCOPE AND METHOD OF PHOTOGRAPHING TEM IMAGES

BACKGROUND OF THE INVENTION

1. Field of the Invention

The present invention relates to an electron microscope having a function of photographing TEM (transmission electron microscope) images of specimens and to a method of photographing such images in the microscope.

2. Description of the Related Art

Today, electron microscopes utilizing a minimum dose system (MDS) are used to observe specimens that are susceptible to electron beam damage as typified by medical and biological specimens.

The MDS is a method of minimizing the electron beam damage to the field of view to be photographed. Since the damage to the field of view to be photographed occurs mostly during a focusing operation performed prior to photography, the focusing operation is done outside the field of view in this minimum dose system.

The minimum dose system is described in further detail. This system involves three modes of operations, i.e., SEARCH mode, FOCUS mode, and PHOTO mode.

First, when the electron microscope adopting the minimum dose system is in the SEARCH mode, the second condenser lens is excited strongly as shown in the ray diagram of FIG. 1(a). Therefore, the illuminating electron beam EB is focused above the specimen and hits a wide area of the specimen. Consequently, the electric current per unit area is small. The specimen is less damaged.

The electron beam transmitted through the specimen as a result of this electron beam irradiation enters a magnifying lens system positioned behind the specimen. This lens system projects a TEM image of a wide field of view of the specimen onto a fluorescent screen. Then, an operator operates the specimen holder-moving device to bring the field of view A to be photographed into the center of the fluorescent screen, i.e., onto the optical axis, as shown in the right view of FIG. 1(a).

Then, in FOCUS mode, the second condenser lens is so excited that the illuminating electron beam EB is sharply focused onto the specimen, as shown in FIG. 1(b). The deflector is so controlled that the electron beam EB hits a region B close to the field of view A to be photographed, the field of view A having been selected in the SEARCH mode.

The operator then performs a focusing operation or stigmatic correction while watching the TEM image of the region B shown in the right view of FIG. 1(b) projected on the fluorescent screen at this time. Under this condition, the electron beam impinges on the specimen while focused. Therefore, the current per unit area is large. Damage occurs if the irradiation is done for a long time. However, the size of the irradiated area is suppressed to a minimum. Also, the illuminated position is off the field of view. Therefore, the field of view to be photographed is not damaged.

When focusing at the region B quite close to the field of view to be photographed is completed in this way, photography is performed. During the photography, deflection using the deflector is not done. As shown in FIG. 1(c), the second condenser lens is excited so that the illuminating electron beam EB is focused onto the field of view A to be photographed. A TEM image arising from the electron beam transmitted through the specimen is photographed by a photography means.

The right view of FIG. 1(c) shows an image of the area A taken by the photography means. In this case, the magnifying lens system is set at a magnification higher than in the case of FIGS. 1(a) and 1(b). Under this condition, photography is performed. At this time, the specimen is also damaged but minimally, because almost no electron beam hits the photographed region A except during photography.

As described previously, in the prior art electron microscope utilizing the minimum dose system (MDS), the excitation of the condenser lens is varied greatly when the mode of operation is switched from the SEARCH mode shown in FIG. 1(a) to the FOCUS mode shown in FIG. 1(b).

When the lens excitation varies greatly in this way, the position hit by the electron beam deviates during focusing due to a deflecting field caused by the hysteresis of the magnetic circuit or for other causes. As a result, a focused strong electron beam will hit the field of view to be photographed. This field of view should not be illuminated with the electron beam except during photography. In consequence, the field of view to be photographed will be damaged.

Also, in the SEARCH mode, the intensity of the electron beam falling on the specimen should be weakened as much as possible. In the prior art electron microscope, the electron beam cannot be darkened (i.e., cannot be spread) beyond the limit of excitation of the condenser lens.

SUMMARY OF THE INVENTION

It is an object of the present invention to provide an electron microscope which prevents the electron beam from hitting the field of view to be photographed in its FOCUS mode and can make the brightness of the beam on the specimen lower than heretofore in its SEARCH mode.

It is another object of the present invention to provide a method of photographing a TEM image in this electron microscope.

The former object is achieved in accordance with the teachings of the present invention by an electron microscope comprising: an electron gun for emitting an electron beam; a system of condenser lenses for focusing the electron beam onto a specimen; a deflection means for scanning the focused electron beam on the specimen; a system of magnifying lenses for creating a magnified image of the specimen based on the electron beam transmitted through the specimen as a result of irradiation of the electron beam; and a photography means for performing photography to take a photograph of a TEM image of the specimen magnified and focused by the system of magnifying lenses. This electron microscope is characterized in that it further includes a controller for focusing the system of condenser lenses to focus the electron beam emitted from the electron gun onto the specimen during a search operation conducted to search for a desired field of view prior to the aforementioned photography. Also, the control means controls the deflection means so that the focused electron beam scans the specimen in two dimensions.

Other objects and features of the invention will appear in the course of the description thereof, which follows.

DESCRIPTION OF THE PREFERRED EMBODIMENTS

Figure 2:
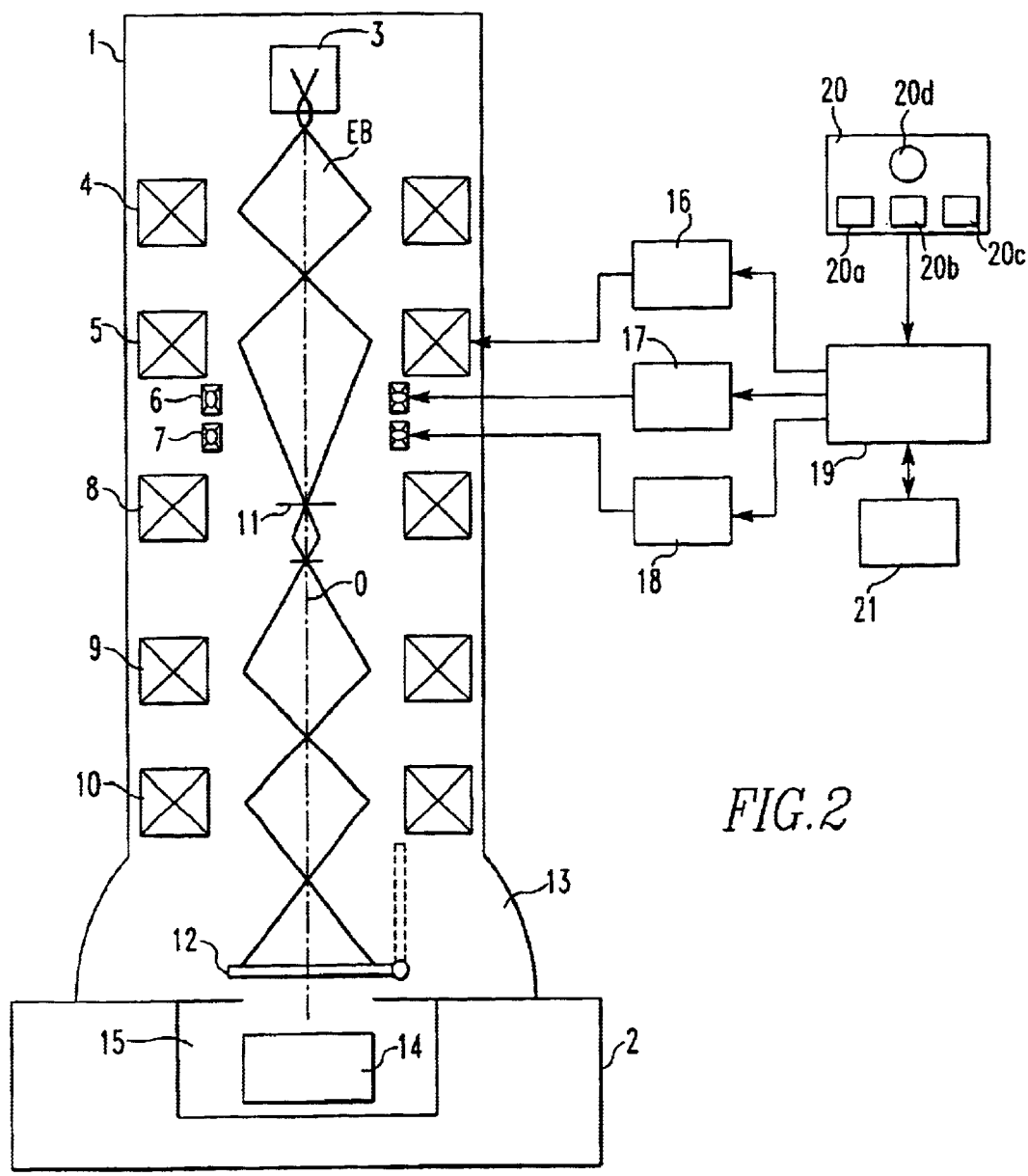
FIG. 2 is a block diagram of an electron microscope in accordance with the present invention.

Referring to FIG. 2, there is shown an electron microscope embodying the concept of the present invention. The structure of this instrument is first described.

The instrument shown in FIG. 2 has a microscope column 1 supported on a pedestal 2. Mounted inside this microscope column 1 are various electron-optical components. That is, an electron gun 3, a first condenser lens 4, a second condenser lens 5, a stigmator coil 6, deflection coils 7, an objective lens 8, an intermediate lens 9, and a projector lens 10 are placed in this order from above. A specimen 11 is positioned between the upper and lower polepieces (not shown) of the objective lens 8. An air core coil is used as each deflection coil 7, and these deflection coils 7 are made of a material that exhibits no hysteresis.

A fluorescent screen 12 is positioned within an image observation chamber 13 behind the projector lens 10. This fluorescent screen 12 can be brought onto the optical axis O (closed) as indicated by the solid line in FIG. 2 and retracted from the optical axis O (opened) as indicated by the broken line.

A photography device 14 is loaded with photographic film or the like, and is placed in a photography chamber 15 located behind the image observation chamber 13.

The instrument further includes a condenser lens control circuit 16, a stigmator coil control circuit 17, and a deflection coil control circuit 18. The condenser lens control circuit 16 controls the amount of the current flowing through the second condenser lens 5. The stigmator coil control circuit 17 controls the amount of the current flowing through the stigmator coil 6. The deflection coil control circuit 18 controls the amount of the current flowing through the deflection coils 7.

These control circuits 16, 17, and 18 are connected with a central control device 19. A control panel 20 and a memory 21 are also connected with the central control device 19. The control panel 20 has a field-of-view search switch 20a, a focusing switch 20b, a photography switch 20c, and a brightness control knob 20d.

In the instrument of FIG. 2, the interior of the microscope column and the interior of the photography chamber are evacuated to a high vacuum by an evacuating system (not shown). The structure of the electron microscope of FIG. 2 has been described thus far. The operation is next described.

First, an operator depresses the field-of-view search switch 20a on the control panel 20 to search the specimen 11 for a field of view of interest. Then, the central control device 19 sends an excitation signal $C_0$ to the condenser lens control circuit 16 to excite the second condenser lens 5 to the same state as the state of excitation assumed during photography as described later. In particular, this excitation signal $C_0$ acts to sharply focus the electron beam EB onto the specimen 11 as shown in FIG. 2, the beam EB having been generated by the electron gun 3 and focused by the first condenser lens 4.

If the field-of-view search switch 20a is depressed, the central control device 19 sends a scan signal $S_0$ to the deflection coil control circuit 18 to scan the electron beam EB across a scanned area $w_0$ ($x_0 \times y_0$) at a scan speed so in two dimensions. If an afterimage is formed on the fluorescent screen, the scan speed $s_0$ in the vertical direction is such that one scan is completed in less than 100 ms. The scan speed in the horizontal direction is approximately (scan speed in the vertical direction)/(number of scanning lines in the horizontal direction). At this time, the electron beam scan direction $S_D$ is the x-direction, for example.

If the field-of-view search switch 20a is depressed, the central control device 19 produces a stigmation signal Stig to the stigmator coil control circuit 17 to produce astigmatism that elongates the cross section of the beam in a direction vertical to the electron beam scan direction $S_D$ (in this case, the y-direction).

Data about the excitation signal $C_0$, scan signal $S_0$, and stigmation signal Stig has been previously stored in the memory 21. If the field-of-view search switch 20a is depressed, the central control device 19 reads the data about these signals and supplies these signals to the control circuits 16, 17, and 18 as mentioned previously.

Figure 3:
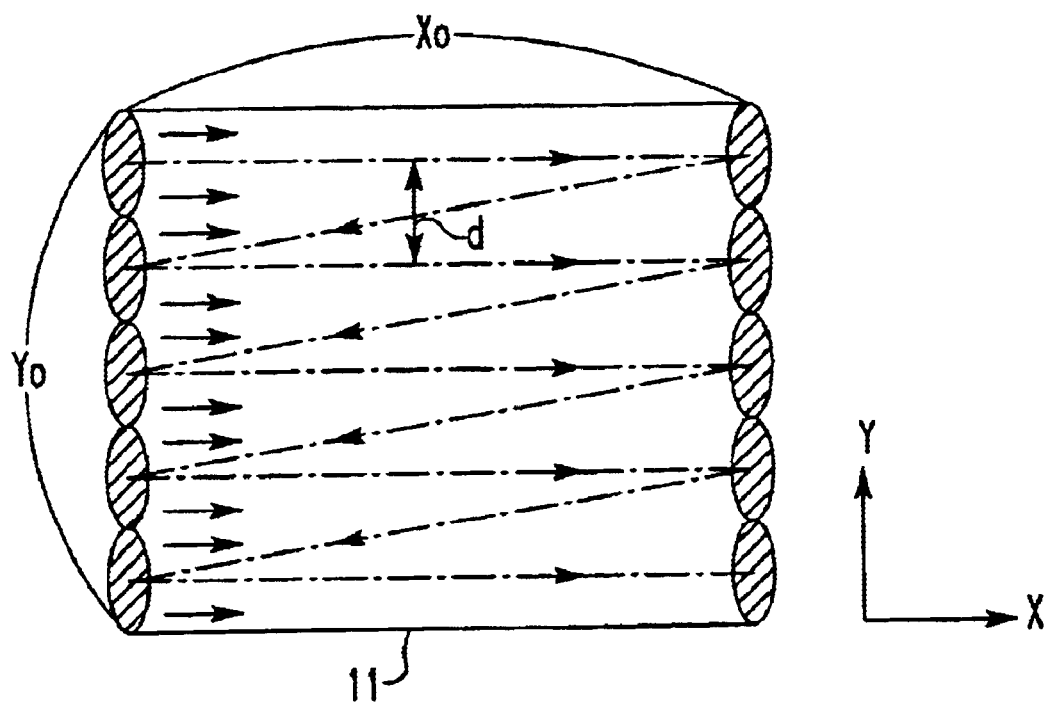
FIG. 3 is a diagram illustrating the operation of the instrument shown in FIG. 2.

The condenser lens control circuit 16 controls the value of the current flowing through the second condenser lens 5 according to the excitation signal $C_0$. The deflection coil control circuit 18 controls the value of the current flowing through the deflection coils 7 according to the scan signal $S_0$. The stigmator coil control circuit 17 controls the value of the flowing through the stigmator coil 6 according to the stigmation signal Stig. As a result of these control operations, the area $w_0$ ($x_0 \times y_0$) on the specimen 11 is scanned in two dimensions by the focused electron beam EB having astigmatism in the y-direction, as shown in FIG. 3.

The astigmatism is intentionally given to the beam EB in a direction (y-direction) perpendicular to the electron beam scan direction to illuminate a wide area on the specimen with the beam with one line scan in the x-direction. As this astigmatism is generated, the spacing d between the scanning lines of the electron beam EB is set almost equal to the width of the electron beam EB in the y-direction.

The electron beam transmitted through the specimen as a result of the electron beam scanning as described above is magnified and focused by the system of magnifying lenses consisting of the objective lens 8, the intermediate lens 9, and the projector lens 10. A TEM image of a wide area of the specimen is projected onto the fluorescent screen 12 that is in a closed state. The operator operates a specimen holder-moving mechanism (not shown) to move the specimen 11 such that the field of view to be photographed is brought into the center of the fluorescent screen, i.e., onto the optical axis O.

Figure 4A:
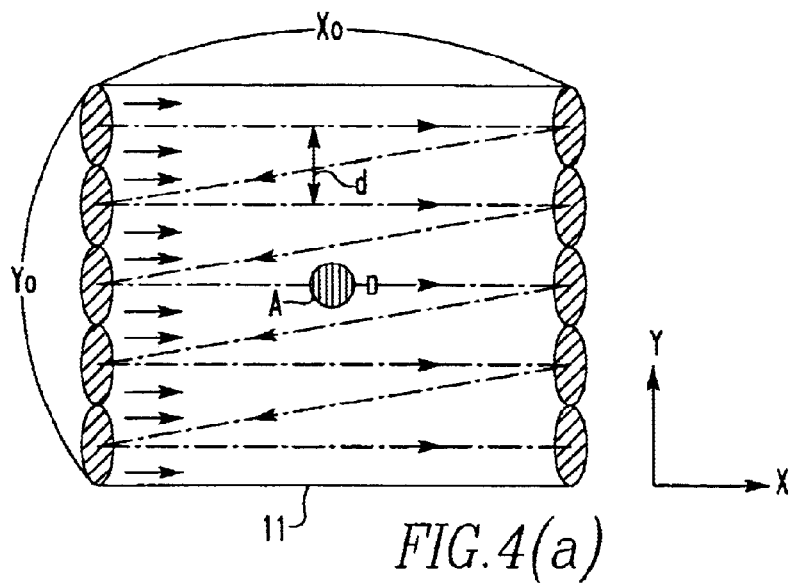
FIGS. 4(a) and 4(b) are diagrams illustrating the operation of the instrument shown in FIG. 2.
Figure 4B:
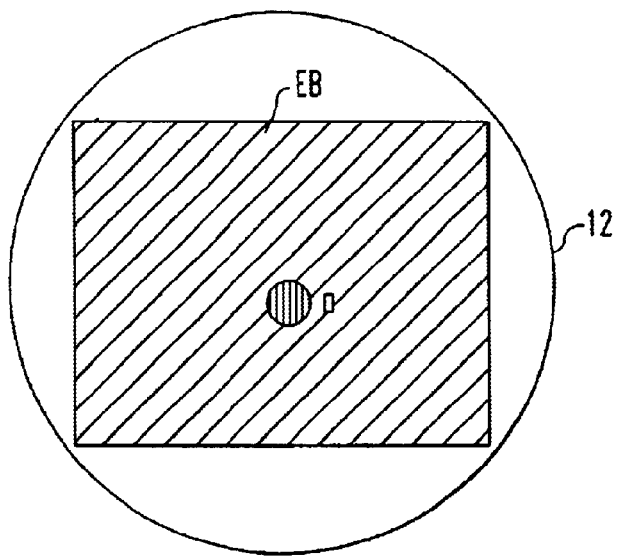

FIG. 4(a) shows the manner in which the specimen is being scanned with the electron beam after the specimen has been moved. The specimen is being scanned with the beam about the selected field of view A to be photographed. FIG. 4(b) shows an image projected onto the fluorescent screen at this time. Where the image should be projected onto the whole fluorescent screen, the magnification of the system of magnifying lenses or the electron beam scanning interval is increased.

When the search for the field of view to be photographed is completed in this way, the operator then depresses the focusing switch 20b on the control panel 20 to perform a focusing operation. The central control device 19 sends a deflection signal $S_B$ to the deflection coil control circuit 18 to direct the electron beam EB to an area B slightly apart from the photographed area A selected in the SEARCH mode. That is, the area B is slightly outside of a point on the specimen through which the optical axis passes. Data about this deflection signal $S_B$ has been previously stored in the memory 21. When the focusing switch 20b is depressed, the control device 19 reads data about the deflection signal $S_B$ from the memory 21 and supplies the signal to the deflection coil control circuit 18.

When the focusing switch 20b is depressed, the central control device 19 continues the supply of the excitation signal $C_0$ to the condenser lens control circuit 16 but cuts off the supply of the stigmation signal Stig to the stigmator coil control circuit 17.

Figure 1A:
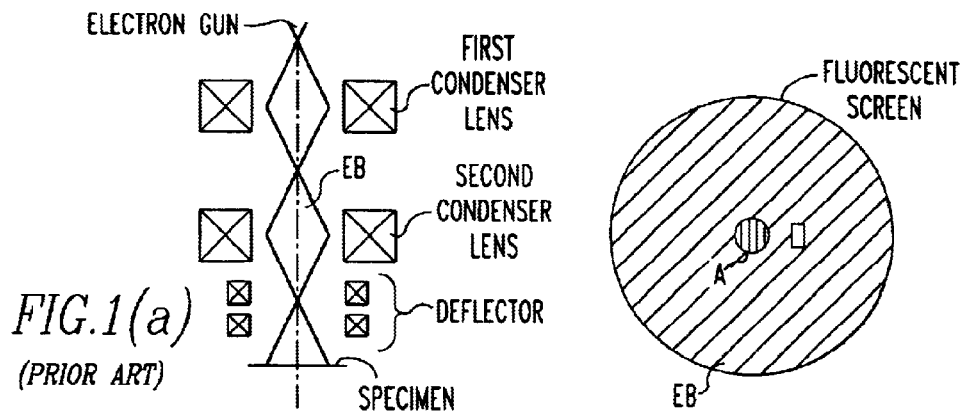
FIGS. 1(a), 1(b), and 1(c) are views illustrating the prior art method of photographing a TEM image.
Figure 1B:
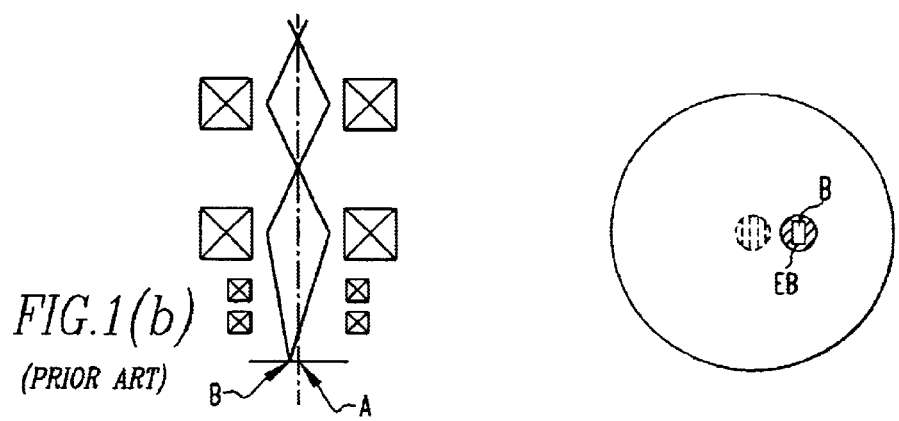
Figure 5:
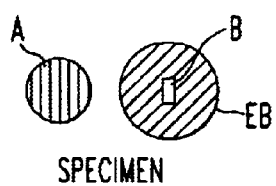
FIG. 5 is a diagram illustrating the operation of the instrument shown in FIG. 2.

As a result of the control sequence described thus far, the focused electron beam EB of circular cross section strikes the area B outside of the photographed area A on the specimen 11, as shown in FIG. 5. The operator adjusts the state of excitation of the objective lens 8 to focus the beam or adjusts the state of excitation of the stigmator coil (not shown) mounted inside the objective lens 8 to stigmate the image while watching the TEM image projected on the fluorescent screen at this time as shown in FIG. 1(b).

When the focusing operation in the area B quite close to the photographed field of view or stigmation correction is completed in this way, the operator depresses the photography switch 20c on the control panel 20.

The central control device 19 sends a deflection signal (blanking signal) to the deflection coil control circuit 18 to deflect the electron beam EB away from the specimen for a given time T, for minimizing the thermal drift caused by the electron beam irradiation of the specimen 11. The central control device 19 controls a fluorescent screen driver device (not shown) to open the fluorescent screen 12. Also, the central control device 19 controls a shutter driver device (not shown) to bring a shutter (not shown) onto the optical axis O, the shutter being located between the fluorescent screen and the projector lens.

The central control device 19 continues the supply of the excitation signal $C_0$ to the condenser lens control circuit 16. When the given time T elapses, the central control device 19 cuts off the supply of the blanking signal to the deflection coil control circuit 18 and controls the shutter driver device to retract the shutter off the optical axis O.

Figure 1C:
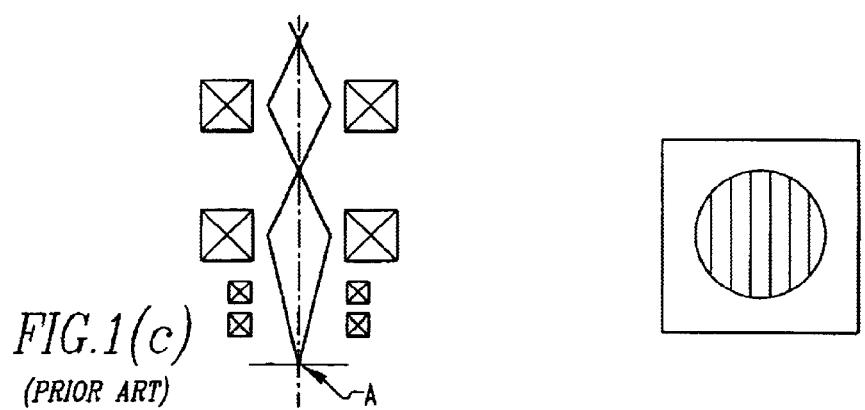

As a result of the control sequence described thus far, the electron beam EB focused by the second condenser lens 5 hits the field of view A on the specimen to be photographed as shown in FIG. 1(c). A TEM image created by the electron beam transmitted through the photographed field of view A is magnified by the system of magnifying lenses at a desired magnification and exposed to photographic film on the photography device 14 for a given time.

While the operations of the electron microscope shown in FIG. 2 starting with search for a desired field of view and ending with photography have been described thus far, the electron beam is scanned during the search to obtain a TEM image in this microscope. The state of excitation of the second condenser lens does not vary during the sequence of operations starting with the search and ending with photography. Therefore, if the mode of operation of the instrument is switched from SEARCH mode to FOCUS mode, any deflecting field which would have been heretofore produced by hysteresis is not generated. Consequently, during the FOCUS mode, the focused intense electron beam does not erroneously hit the field of view to be photographed, unlike the prior art. Since the field of view to be photographed is not damaged prior to photography, good photography of the specimen can be performed.

In the electron microscope of FIG. 2, the area $w_0$ on the specimen scanned with the electron beam during the SEARCH mode is made wider than the conventional illuminated area when the condenser lens is excited maximally. In consequence, specimen damage during the SEARCH mode can be suppressed compared with the case in which the prior art technique is used. If this scanned area $w_0$ is set equal to the conventional maximum illuminated area described above, the damage to the specimen due to the electron beam irradiation will be almost the same as where the prior art technique is used. Where an electron beam scanning method is utilized as in the present invention, if the specimen is not conductive and is tilted, the tendency that the specimen is moved by a charging effect can be suppressed.

In the electron microscope of FIG. 2, if the brightness control knob 20d is operated, the area scanned with the electron beam can be varied at will during the SEARCH mode. In the instrument of FIG. 2, the beam diameter remains unchanged if the scanned area is increased. Since the number of scanning lines during one frame scan time is increased, the scan speed of the electron beam can be increased. As a result, the image can be observed with less flicker.

While the electron microscope of FIG. 2 has been described thus far, the present invention is not limited to this embodiment. For example, in the above embodiment, an astigmatic electron beam is directed to the specimen during the SEARCH mode. A non-astigmatic focused electron beam of circular cross section may be directed to the specimen. Furthermore, in the above embodiment, a TEM image is exposed to photographic film. The TEM image may be photographed using a TV camera or the like.

Having thus described my invention with the detail and particularity required by the Patent Laws, what is desired protected by Letters Patent is set forth in the following claims.

What is claimed is:

1. An electron microscope comprising:
   an electron gun for emitting an electron beam;
   a system of condenser lenses for focusing said electron beam onto a specimen;
   a deflection means for scanning the focused electron beam on the specimen;
   a system of magnifying lenses for creating a magnified image of said specimen based on the electron beam transmitted through the specimen as a result of irradiation of the electron beam;
   a photography means for performing photography to take a photograph of a TEM image of the specimen magnified and focused by said system of magnifying lenses; and
   a control means for controlling said system of condenser lenses to focus the electron beam emitted from said electron gun onto said specimen during a search operation conducted to search for a field of view to be photographed prior to said photography, for controlling said deflection means so that the focused electron beam scans said specimen in two dimensions during said search operation, and for controlling said deflection means so that said focused electron beam irradiates an area outside of said field of view to be photographed on the specimen during a focusing operation or stigmatic correction prior to said photography.

2. The electron microscope of claim 1, wherein there is further provided a stigmatic correction means, and wherein said control means controls said stigmatic correction means in such a way that the electron beam on the specimen has astigmatism that elongates the cross section of said electron beam in a direction perpendicular to the direction of scanning.

3. The electron microscope of claim 1, wherein the state of excitation of said system of condenser lenses assumed during said search operation is the same as the state of excitation of said system of condenser lenses assumed during said focusing operation or stigmatic correction.

4. The electron microscope of claim 3, wherein the state of excitation of said system of condenser lenses assumed during said search operation is the same as the state of excitation of said system of condenser lenses assumed during said focusing operation or stigmatic correction.

5. The electron microscope of claim 1, 2, or 3, wherein an air core coil or coils are used as said deflection means.

6. A method of photographing a transmission electron microscope (TEM) image of a specimen, using an electron microscope having an electron gun for emitting an electron beam, a system of condenser lenses for focusing said electron beam onto a specimen, a deflection means for scanning the focused electron beam on the specimen, a system of magnifying lenses for creating a magnified image of said specimen based on the electron beam transmitted through the specimen as a result of irradiation of the electron beam, and a photography means for performing photography to take a photograph of a TEM image of the specimen magnified and focused by said system of magnifying lenses, said method comprising the steps of:

focusing said electron beam emitted from said electron gun onto the specimen, scanning the focused electron beam across the specimen in two dimensions, and determining a field of view on the specimen to be photographed using a TEM image created by the electron beam transmitted through the specimen at this time;

focusing the electron beam off said field of view to be photographed on the specimen and performing a focusing operation or stigmatic correction using a TEM image created by the electron beam transmitted through the specimen; and focusing the electron beam onto said field of view to be photographed and taking a photograph of the TEM image created by the electron beam transmitted through the specimen.

7. A method of photographing a transmission electron microscope (TEM) image as set forth in claim 6, wherein the state of excitation of said system of condenser lenses assumed during the step of determining the field of view is the same as the state of excitation of said system of condenser lenses assumed during said focusing operation or stigmatic correction.

8. A method of photographing a transmission electron microscope (TEM) image as set forth in claim 6, wherein said electron microscope further includes a stigmatic correction means, and wherein said step of scanning the focused electron beam across the specimen in two dimensions uses an electron beam having astigmatism that elongates the cross section of the electron beam in a direction vertical to the scanning direction of the electron beam.

9. An electron microscope comprising:
an electron gun for emitting an electron beam;
a system of condenser lenses for focusing said electron beam onto a specimen;
a deflection means for scanning the focused electron beam on the specimen;
a system of magnifying lenses for creating a magnified image of said specimen based on the electron beam transmitted through the specimen as a result of irradiation of the electron beam;
a display means for displaying a TEM image of the specimen magnified and focused by said system of magnifying lenses; and
a control means for controlling said system of condenser lenses to focus the electron beam emitted from said electron gun onto said specimen during a search operation conducted to search for a field of view to be displayed prior to said display, for controlling said deflection means so that the focused electron beam scans said specimen in two dimensions during said search operation, and for controlling said deflection means so that said focused electron beam irradiates an area outside of said field of view to be displayed on the specimen during a focusing operation or stigmatic correction prior to said display.

10. The electron microscope of claim 9, wherein there is further provided a stigmatic correction means, and wherein said control means controls said stigmatic correction means in such a way that the electron beam on the specimen has astigmatism that elongates the cross section of said electron beam in a direction perpendicular to the direction of scanning.

11. The electron microscope of claim 9, 4, or 10, wherein an air core coil or coils are used as said deflection means.

12. A method of photographing a transmission electron microscope (TEM) image of a specimen, using an electron microscope having an electron gun for emitting an electron beam, a system of condenser lenses for focusing said electron beam onto a specimen, a deflection means for scanning the focused electron beam on the specimen, a system of magnifying lenses for creating a magnified image of said specimen based on the electron beam transmitted through the specimen as a result of irradiation of the electron beam, and a display means for performing photography to take a photograph of a TEM image of the specimen magnified and focused by said system of magnifying lenses, said method comprising the steps of:

focusing said electron beam emitted from said electron gun onto the specimen, scanning the focused electron beam across the specimen in two dimensions, and determining a field of view on the specimen to be displayed using a TEM image created by the electron beam transmitted through the specimen at this time;

focusing the electron beam off said field of view to be displayed on the specimen and performing a focusing operation or stigmatic correction using a TEM image created by the electron beam transmitted through the specimen; and focusing the electron beam onto said field of view to be displayed and displaying the TEM image created by the electron beam transmitted through the specimen.

13. A method of displaying a transmission electron microscope (TEM) image as set forth in claim 12, wherein the state of excitation of said system of condenser lenses assumed during the step of determining the field of view is the same as the state of excitation of said system of condenser lenses assumed during said focusing operation or stigmatic correction.

14. A method of photographing a transmission electron microscope (TEM) image as set forth in claim 12, wherein said electron microscope further includes a stigmatic correction means, and wherein said step of scanning the focused electron beam across the specimen in two dimensions uses an electron beam having astigmatism that elongates the cross section of the electron beam in a direction vertical to the scanning direction of the electron beam.

* * * * *